United States Patent

Rosenheimer et al.

Patent Number: 5,817,009
Date of Patent: Oct. 6, 1998

[54] ARRANGEMENT FOR NONINVASIVE DETERMINATION OF THE OXYGEN SATURATION IN HUMAN BLOOD VESSELS OR ORGANS

[75] Inventors: Michael N. Rosenheimer, Hattenhofen; Sandra Gruenwald, Munich, both of Germany

[73] Assignee: MIPM Mammendorfer Institut fuer Physik und Medizin GmbH, Hattenhofen, Germany

[21] Appl. No.: 643,630

[22] Filed: May 6, 1996

[51] Int. Cl.$^6$ ........................................................ A61B 5/00
[52] U.S. Cl. ............................................................. 600/339
[58] Field of Search .................................... 600/323, 326, 600/327, 339, 340, 341, 338

[56] References Cited

U.S. PATENT DOCUMENTS

| | | | |
|---|---|---|---|
| 4,899,757 | 2/1990 | Pope et al. | |
| 5,181,517 | 1/1993 | Hickey | 600/846 |
| 5,228,440 | 7/1993 | Chung et al. | 600/339 |
| 5,247,932 | 9/1993 | Chung et al. | 600/338 |
| 5,357,954 | 10/1994 | Shigezawa et al. | 600/339 |
| 5,417,207 | 5/1995 | Young et al. | 600/323 |

FOREIGN PATENT DOCUMENTS 3211003  10/1983  Germany .

OTHER PUBLICATIONS

Sinclair Yee, et al —"A Proposed Miniature Red/Infrared Oximeter Suitable for Mounting on a Catheter Tip"–IEEE Transactions and Biomedical Engineering, 1997, vol. BME–24, pp. 195–197.

*Primary Examiner*—Jennifer Bahr
*Assistant Examiner*—Eric F. Winakur
*Attorney, Agent, or Firm*—McAulay Nissen Goldberg Kiel & Hand, LLP

[57] ABSTRACT

Arrangement for determining the oxygen saturation in human blood vessels and organs with a measurement sensor with at least two light sources of different wavelengths—preferably wavelengths of 660 nm and 940 nm—and with at least one receiver which receives the light transmitted and reflected from the oxygen particles which are bonded with the hemoglobin in the irradiated vessel or organ and transmits it as an electrical signal to a pulsoximeter for evaluation of the measurement results and readout on a display device. An additional measurement sensor is associated with the measurement sensor for locating a blood vessel or organ to be selected and the two measurement sensors are designed such that they can be handled together as a constructional unit.

13 Claims, 3 Drawing Sheets

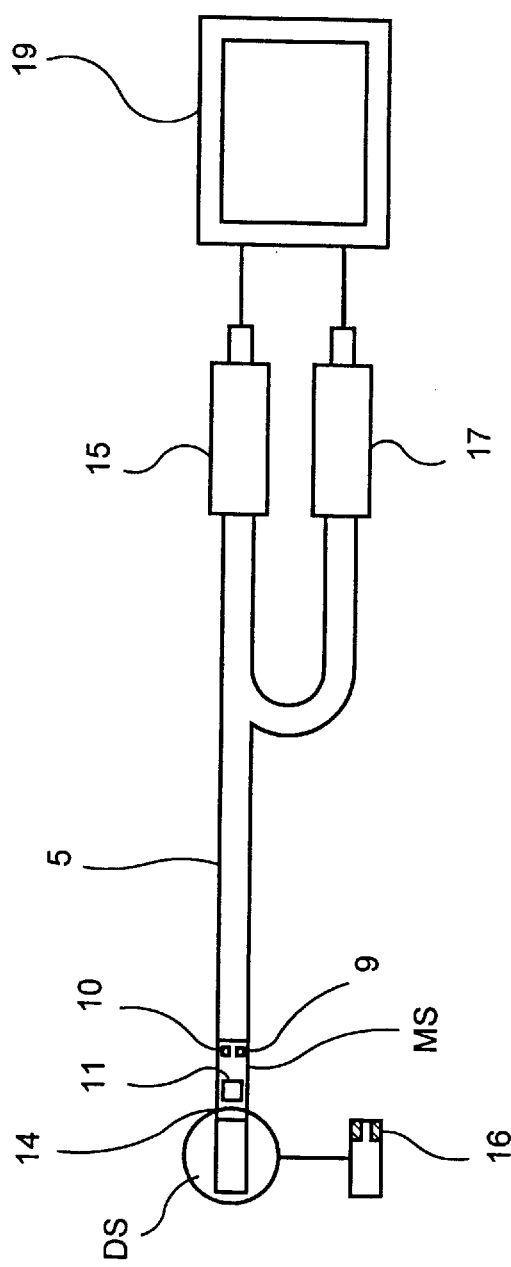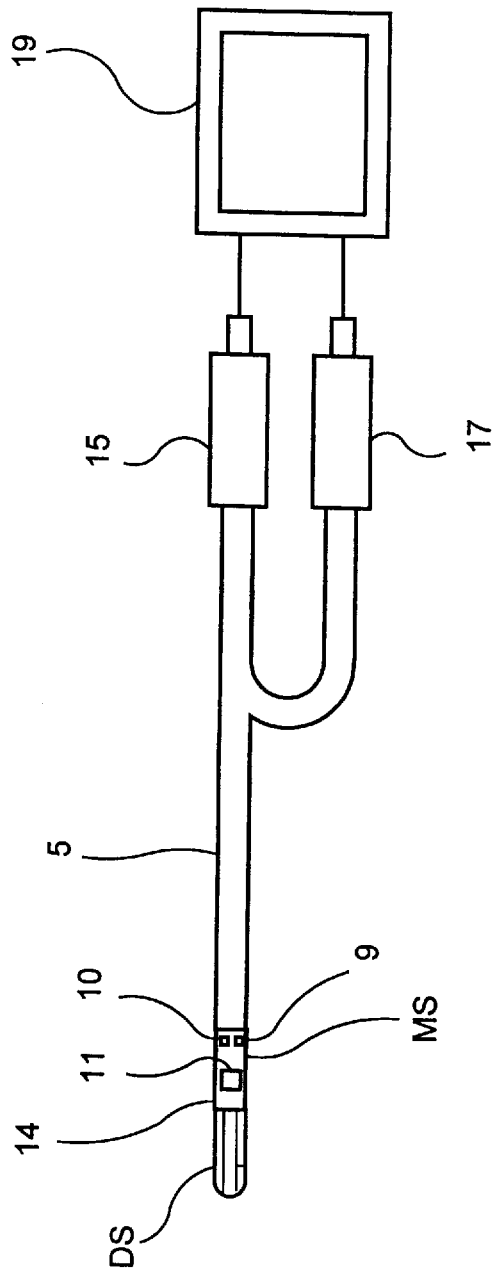

ARRANGEMENT FOR NONINVASIVE DETERMINATION OF THE OXYGEN SATURATION IN HUMAN BLOOD VESSELS OR ORGANS

BACKGROUND OF THE INVENTION

1. Field of the Invention

The invention is directed to an arrangement for determining the oxygen saturation in human blood vessels and organs with a measurement sensor with at least two light sources of different wavelengths—preferably wavelengths of 660 nm and 940 nm—and with at least one receiver which receives the light transmitted and reflected from the oxygen particles which are bonded with the hemoglobin in the irradiated vessel or organ and transmits it as an electrical signal to a pulsoximeter for evaluation of the measurement results and display on a display device.

2. Description of the Related Art

It is known to determine the oxygen content of blood in human blood vessels by means of pulse oximetry. Generally, two light sources and a receiver are used for this purpose. The light sources, e.g., diodes, preferably emit light with a wavelength of 660 nm (red region) and 940 nm (infrared region). The receiver receives the emitted light waves which are reflected or transmitted from the tissue. The light received by the receiver, e.g., a photodetector, is transmitted as an electrical signal to a pulsoximeter. The pulsoximeter evaluates these signals and displays a measurement value proportional to the existing oxygen content on a display device connected with the pulsoximeter.

Catheters are introduced at the measurement site via punctures and natural body orifices in order to access the measurement point. Light guides for the light sources and the receiver are provided in the catheter and terminate at the distal end of the catheter.

Problems are known to occur when using such catheters, e.g., in right heart catheter measurement. In order to stabilize a life-threatening condition, e.g., after a heart attack, the heart function must occasionally be monitored invasively. For this purpose, due to the large diameter of the catheter, one of the large veins (subclavian or jugular vein) must be punctured by the Seldinger technique. A balloon catheter (Swan Ganz catheter) is then floated into the blood stream through this puncture. In so doing, known techniques are employed when working in the direction of the flow of blood. Puncture and the subsequent feeding of the catheter into the blood vessel may lead to damage to the vessel wall with the possibility of ongoing dissection, perforation, thrombosis, triggering of emboli, and sometimes to formation of pseudoaneurysms or arteriovenous fistulae at the puncture site itself. It is often necessary to operate in order to correct these complications.

There is a high risk of complications in both methods. Puncture and the subsequent feeding of the catheter into the blood vessel may lead to damage or perforation of the vessel wall, especially along branches and curvatures of the vessel and potentially along the vessel wall. Further, there is a risk that movement of the catheter will cause mechanical dislodging of deposits at the vessel walls which can result in thromboses and emboli.

In addition, heart irritation occurs, which can trigger cardiac arrhythmia and fibrillation when the catheter contacts the heart muscles. This fibrillation can sometimes not be brought under control therapeutically even when exercising great care. In order to avert heart failure, which is consequently at risk, electric shocks are administered to the patient in this critical state by the use of a defibrillator which cause severe physical stress aside from the disadvantageous autonomic effects.

The measurement itself requires that the catheter position not be disturbed by movement during measurement so as to rule out falsified measurement results and to ensure reproducible measurement. However, undesirable falsification of readings occurs in this method precisely in the vicinity of the beating heart, since the strong pressure fluctuations in the catheter resulting from heart activity cannot be curbed during measurement. Therefore, it is also difficult to achieve reproducibility for comparison measurements.

Although the catheter with the measuring sensor could also be introduced into the vicinity of the pulmonary artery through the esophagus, it is practically impossible to locate the pulmonary artery with the required accuracy, since the physician performing the procedure has no indication as to which of the numerous arteries containing oxygen-rich blood is to be used for the actual measurement of the oxygen content. Accordingly, it is not guaranteed that the measurement will actually be carried out at the pulmonary artery. Such measurement results do not allow the treating physician to arrive at a diagnosis with certainty and to implement appropriately informed therapy. For this reason, it is also not possible to make comparisons with other measurement results based on values drawn from medical experience.

The oxygen content of deeper vessels and organs cannot be measured externally with the known measurement sensors.

There is a substantial need for an arrangement which allows the oxygen content of blood vessels, particularly the pulmonary artery and deeper vessels or organs, to be identified with certainty and the oxygen content of the selected vessel to be measured without resorting to high-risk arterial or venous access, since this was previously done invasively.

OBJECT AND SUMMARY OF THE INVENTION

It is the primary object of the present invention to remedy this situation by providing an arrangement which makes it possible to measure the oxygen content in blood vessels without having to perform invasive procedures (puncture) on the patient and in which the region of the measurement location of the blood vessel selected for measurement can be reliably located with the entire arrangement without risk and in a reproducible manner and the measurement locations can be displayed on a display device.

This object is met according to the invention in that an additional measurement sensor is associated with the measurement sensor for locating a vessel or organ to be selected and the two measurement sensors are designed to be handled together as a constructional unit.

According to a first embodiment example of the invention, a sonography transmitter-receiver which emits ultrasonic waves is associated with the measurement sensor for locating, the emitted ultrasonic waves and the light waves from the light sources travel in substantially the same direction, and the measurement sensor and sonography transmitter-receiver are combined in a catheter forming a sensor unit.

In the invention, the measurement sensor according to the first embodiment example is combined with a sonography transmitter-receiver emitting ultrasonic waves so as to enable a precise positioning after introducing the measurement arrangement through the mouth and the pharynx into the alimentary canal.

A further advantage of the measurement sensor which is outfitted with the sonography transmitter-receiver emitting ultrasonic waves consists in the unadulterated reproducibility of the measurement results, since the measurement site can be located with certainty by means of the probe emitting ultrasonic waves and all measurements accordingly depend exclusively on the actual oxygen content of the blood in the irradiated blood vessel or organ of the patient and the measurement results are not affected by the selection of incorrect measurement sites. In addition, the arrangement according to the invention also ensures that the measurement site is monitored during the measurement.

Disadvantageous interference in the measurement of the oxygen content in the selected vessel or organ due to the beating of the heart or due to blood flow is extensively eliminated. When the arrangement is located in the esophagus, for example, during measurement, falsification of the measurement results will not occur because so-called movement artifacts are reduced.

According to another embodiment form of the invention, the light sources and the receiver are detachably connected with the sonography transmitter-receiver or the sonography transmitter-receiver is rigidly connected with the light sources and the receiver and is integrated at the distal end of the catheter carrying the pulse oximetry sensor.

According to a second embodiment example, deeper vessels can also be specifically selected and their oxygen content can be measured in that the measurement sensor has two beam paths of two light-generating and light-transmitting systems, which beam paths are swivelable at an angle to a vertical axis, and the systems intersect at a point on the vertical axis and at least one shared receiver is associated with these two systems.

For this purpose, each light-generating and light-conducting system advantageously comprises, within a tube, an objective lens, collimating objective lenses, and light sources which can be adjusted and fixed relative to one another. The tube has a hinge joint in the region of the objective lens and the receivers are arranged parallel to the vertical axis in a receiver housing having hinge joints which are arranged symmetrically with respect to the vertical axis. A system generating and conducting red light and a system generating and conducting infrared light are supported in the respective hinge joint of the receiver housing so as to be swivelable relative to the vertical axis and can be adjusted at an angle to the vertical axis by adjusting means and fixed by clamping means. Finally, a flexible cover for screening out extraneous light is associated with the light-generating and light-conducting systems and with the receivers.

When measuring the oxygen saturation with this embodiment form of the invention, which can be done from any point on the body, invasive procedures are avoided so that physical and psychic side-effects on the patient are substantially reduced. Other risk factors such as heart irritation or perforations are avoided by the arrangement according to the invention.

Additional features of the invention are indicated in the subclaims.

The invention is described in the following with reference to three embodiment examples which are shown more or less schematically in the drawings.

BRIEF DESCRIPTION OF THE DRAWINGS

FIG. 2 shows a section through a second embodiment example of the invention, according to FIG. 1, with two light-emitting diodes, a receiver, and a sonography transmitter-receiver placed thereon which are associated with the common distal end of a catheter;

FIG. 3 shows a section through a third embodiment example of the invention, according to FIG. 1, with the same component parts as in FIG. 1, but with an integral construction comprising the measurement sensor and the sonography transmitter-receiver at the distal end of the catheter.

DESCRIPTION OF THE PREFERRED EMBODIMENTS

Figure 1:
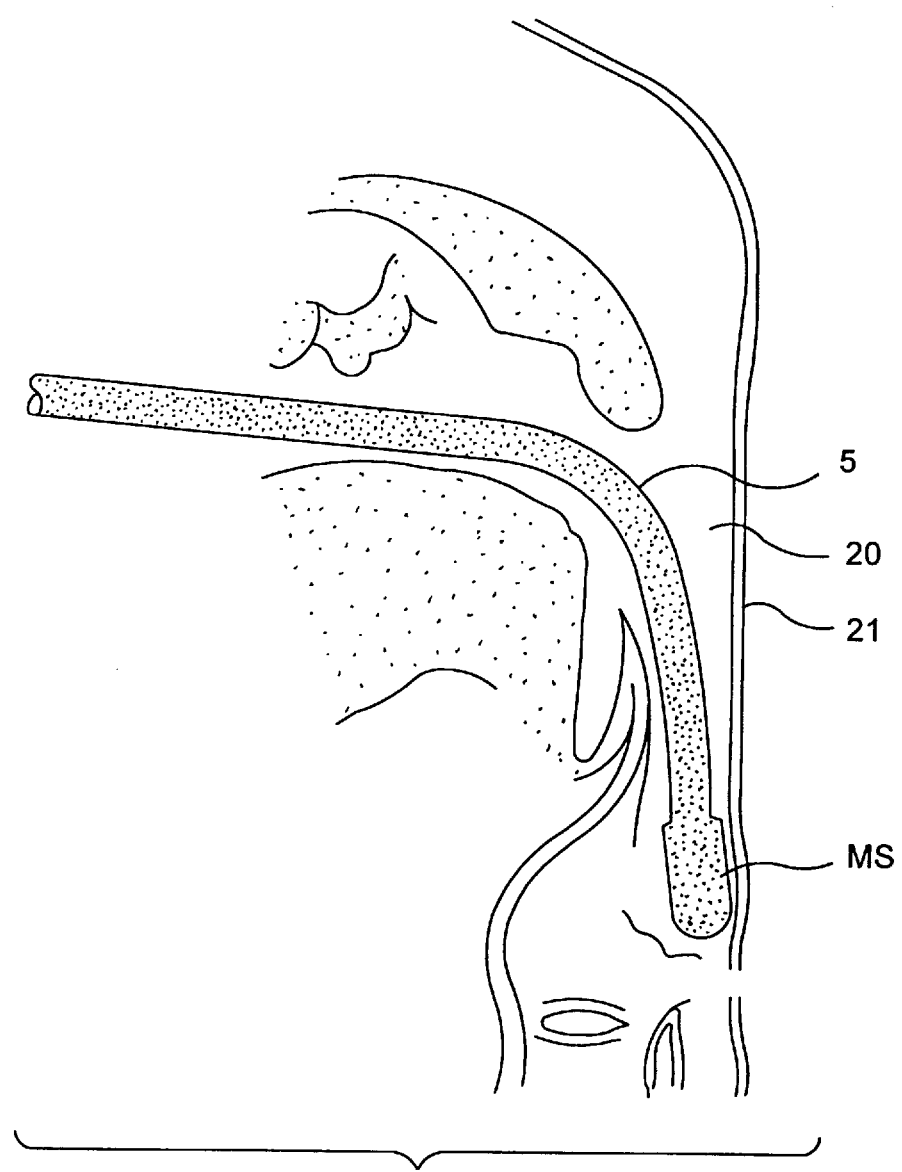
FIG. 1 shows the arrangement according to the invention with a measurement sensor for intraesophageal application.

FIG. 1 shows a flexible catheter 5, known per se in medical science, which is provided with a measurement sensor MS, to be described hereinafter, and which is shown introduced into the human alimentary canal 20. The measurement sensor MS is only shown schematically and is located in the illustrated position at an intraesophageal measurement site 21.

Arranged in the catheter 5 are means, known per se and not shown in the drawing, by which the distal end of the catheter 5 can be guided and positioned when the treating physician introduces the catheter into the alimentary canal 20 of a patient externally, e.g., in order to determine the oxygen content in the pulmonary artery.

As is shown in FIG. 3, the catheter 5 has at the distal end 6 at least two photodiodes 9 and 10 emitting different wavelengths. Photodiode 9 preferably radiates light with a wavelength of 660 nm (red region) and photodiode 10 preferably emits light with a wavelength of 940 nm (infrared region). These different light sources are activated simultaneously or alternately at predetermined time intervals by switching means, not shown, which are arranged in a pulsoximeter 15.

At least one receiver 11, which is likewise arranged at the distal end 6 of the catheter 5, receives the light reflected from the irradiated blood vessel or organ and transmits the light signal outward as a corresponding electrical signal to the pulsoximeter 15 via lines which are accommodated in the catheter 5. Measurement values which are proportional to the oxygen content present at the measurement location in the blood vessel are then calculated from these signals in a known manner in the pulsoximeter 15 and are displayed on a display device 19.

As is well-known, the emitted light is absorbed to varying degrees depending on the oxygen content in the hemoglobin particles contained in the blood flowing through the blood vessel. Hemoglobin particles are either oxygenated or low in oxygen.

Thus, if the hemoglobin particles occurring in the blood are irradiated by two or more different frequencies emitted alternately or simultaneously, the hemoglobin particles absorb the different light wavelengths differently depending on the oxygen content present and a measurable absorption difference will occur, from which the oxygen saturation of the blood at the measurement site can be calculated.

A sonography transmitter-receiver DS is associated with the distal end 6 of the catheter 5 as is shown in FIG. 3. The sonography transmitter-receiver DS is detachably connected as a removable unit 14 with the distal end 6 of the catheter 5 which is formed of a suitable carrier material The connection between the removable unit 14 and the distal end 6 of the catheter 5 is effected by means of springing clamping plates 16 which are arranged at the catheter or unit 14 and which hold the unit 14 and ensure a secure but detachable connection when connected. The sonography transmitter-receiver DS is so arranged in the region of the distal end of the catheter that the radiation is emitted radially.

When introduced into a natural body orifice, e.g., into the esophagus 20, the positioning of the pulse oximetry sensor MS is effected via the sonography transmitter-receiver DS. The measurement site at which the measurement is carried out is selected by means of the sonography transmitter-receiver DS and the oxygen saturation is then recorded by the pulsoximeter sensor MS in the region of the measurement site and displayed on the display device. The measurement site can be a blood vessel or an organ.

Due to the radial alignment, the ultrasonic waves emitted by the sonography transmitter-receiver DS travel in the same direction toward the axes of the emission maxima of the photodiodes 9 and 10.

The reflection signals of the sonography transmitter-receiver DS are transmitted in a known manner through the catheter 5 to a sonography device 17 so that the ultrasonic waves also send a signal which is displayable on the monitor (not shown) of the sonography device during the actual measurement of the oxygen content in a blood vessel or organ. The treating physician can ensure at all times that the measurement position is maintained during measurement by observing the externally displayed measurement signal.

The embodiment example according to FIGS. 2 and 3 likewise shows a measurement sensor MS and a sonography transmitter-receiver DS at the distal end 6 of a catheter 5. In contrast to the embodiment example according to FIG. 3, the sonography transmitter-receiver DS is integrated in the distal end 6 of the catheter 5, that is, it is connected with the catheter 5 in a stationary manner.

A measurement site can also be located by means of differential pressure spectra of a pressure measurement probe which is connected with the measurement sensor of the sensor unit in place of a sonography transmitter-receiver.

Figure 4:
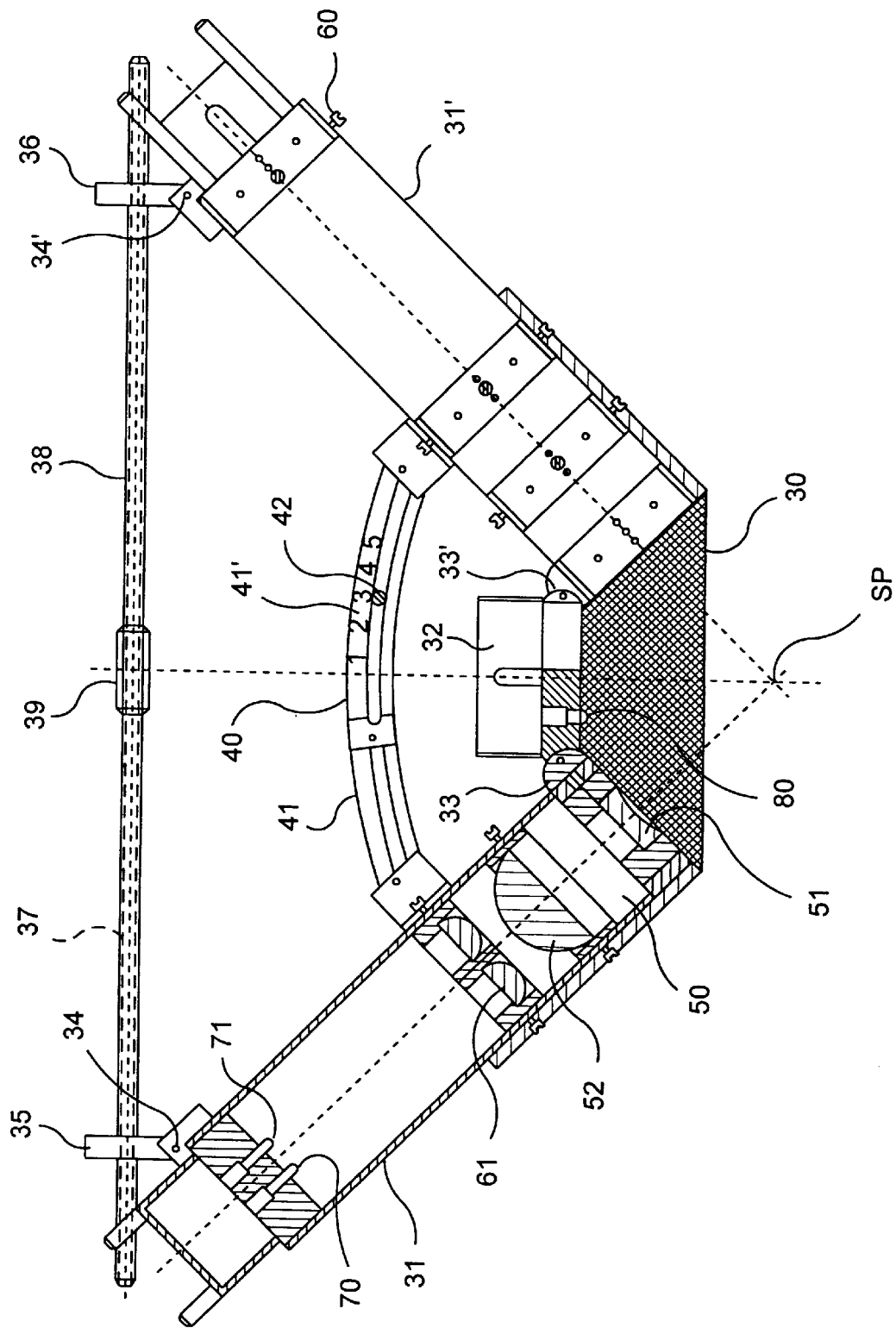
FIG. 4 shows the arrangement according to the invention with a measurement sensor for external application.

Another embodiment form of the measurement sensor MS for external, noninvasive measurement of the oxygen content of deeper measurement locations is shown in FIG. 4. A receiver housing 32 has hinge joints 33 and 33' which are arranged at a distance from one another eccentrically and symmetrically with respect to the vertical axis y and in which a tube 31 and 31' is supported so as to be swivelable with respect to the vertical axis.

Brackets 34 and 34' in which threaded nuts 35 and 36 are supported in an articulated manner are provided at every tube at the ends located opposite to the hinge joints 33 and 33'. The threaded nuts 35 and 36 have left-handed and right-handed threads, respectively, in which the threaded spindles 37 and 38 of an adjusting screw 39 engage for the purpose of changing the angular position of the tubes relative to one another.

The tube 31 which is shown in section in FIG. 4 has, in the region of the hinge joint 33, an objective lens 50 formed of a plano-concave lens 51 arranged at the outlet ends of the tube 31 and a plano-convex lens 52 of greater diameter situated deeper inside the tube 31. The plano-sides of the plano-concave lens 51 and the plano-convex lens 52 face one another and are arranged in an adjustable mounting in the tube 31. On the convex side of the plano-convex lens 52, at least two collimating objective lenses 60 and 61 are held, likewise in an adjustable mounting, in an eccentric arrangement with respect to the optical axis of the objective lens 50. A red light source 70 is associated with the optical axis of the collimating objective lens 60 and a second red light source 71 is associated with the optical axis of the collimating objective lens 61 such that there is a telecentric beam path between the collimating objective lenses 60 and 61 and the imaging objective lens 50. The objective lens unites the beam paths of the collimator objective lenses 60 and 61 and images these beam paths collinearly to infinity. The tube 31' contains the same optical arrangement as the tube 31 described above, but infrared light sources are provided as light sources. Each tube 31 and 31' forms a light-generating and light-transmitting system for red light or infrared light.

A flexible cover 30 of opaque material is associated with the exit openings of the light-generating and light-conducting systems and the entrance opening of the receiver housing in order to screen out extraneous light.

Receivers 80 of suitable spectral sensitivity whose sensitive maxima are aligned approximately parallel to the vertical axis y are provided in the receiver housing 32 eccentrically with respect to the vertical axis y.

The beam bundles which are emitted by the light sources 70 and 71 and projected by the collimators 60 and 61 and the objective lens 50 of each tube 31 and 31', which is swiveled at the same angle alpha to the vertical axis, intersect the downward lengthening of vertical axis y at intersection point SP. By adjusting the adjusting screw 39, the angle of the beam paths of the two light-generating and light-transmitting systems can be adjusted in such a way that the intersection point of the two beam paths is adjustable along the vertical axis y.

In order to measure the oxygen content of a blood vessel situated deeper in the tissue or an organ, the arrangement is placed with the long side of the cover flat against the skin so that the intersection point SP lies in the tissue.

The receivers 80 detect the reflected component of light from the two light-generating and light-transmitting systems and transmit this component as an electrical signal to the pulsoximeter.

By turning the adjusting screw, the intersection point SP along the vertical axis y can be localized on a blood vessel B or organ lying in this region and the oxygen saturation can be measured. The threaded spindles can also be driven by a motor-operated actuating element, e.g., a program-controlled stepper motor, which can be actuated or controlled from a control panel in order to automate the process of locating a measurement site. In a miniaturized version, a piezoelectric actuator can also produce the swiveling movement of the light-generating and light-conducting system.

The tubes 31 and 31' of the light-generating and light-conducting systems can be fixed in the adjusted position by a fastening device 40. The fastening device 40 is formed of two clips 41 and 41', one end of each clip 41 and 41' being connected with the tubes 31 and 31', respectively, in an articulated manner. The clips 41 and 41' are provided with graduated scales and have slots 42 and 42' in which a clamping screw 43 with a corresponding lock nut is arranged.

A sonography transmitter-receiver DS, which is not shown in FIG. 4 for the sake of clarity, can be associated with the measurement sensor MS in accordance with the embodiment examples shown in FIGS. 1, 2 and 3, its radiation direction being arranged with reference to the vertical axis.

While the foregoing description and drawings represent the present invention, it will be obvious to those skilled in the art that various changes may be made therein without departing from the true spirit and scope of the present invention.

What is claimed is:

1. A method for the non-invasive in vivo determination of oxygen saturation in human blood vessels and organs comprising:
   a) providing a first oxygen measurement sensor having at least two light sources of different wavelengths and at least one receiver therefor;
   b) providing a second position measurement sensor which forms a constructional unit with the first oxygen measurement sensor;
   c) locating a specific position external to but adjacent to a predetermined vessel or organ with the second position measurement sensor;
   d) positioning the first oxygen measurement sensor at the specific position and monitoring the position with the second position measurement sensor;
   e) radiating light from the light sources on the blood vessel or organ, such that the light which is transmitted by oxygen particles bonded with hemoglobin in the irradiated blood vessel or organ and reflected by the surrounding tissue is received by the receiver;
   f) converting the reflective light received by the receiver into an electrical signal that is proportional to the intensity of the reflected light;
   g) transmitting the electrical signal to a pulsoximeter to determine the oxygen saturation in the blood vessel or organ.

2. The method of claim 1 wherein the first oxygen measurement sensor generates two beams, each of which is symmetrical at an angle to a vertical axis, these beams intersecting at an intersection point on the vertical axis, and at least one shared receiver is associated with these beams.

3. The method of claim 1 wherein the second position measurement sensor is a sonography transmitter-receiver and wherein said sensor emits ultrasonic waves, said ultrasonic waves and the light radiated from the light sources being emitted in substantially the same direction.

4. A device for carrying out the method of claim 1 comprising a first oxygen measurement sensor having at least two light sources and one receiver, a second position measurement sensor for locating a blood vessel or organ, said second position measurement sensor forming a jointly manipulable constructional unit with the first oxygen measurement sensor, said receiver being connected to a pulsoximeter and said pulsoximeter being connected to a display device.

5. The device according to claim 4, wherein the constructional unit is part of a catheter.

6. The device according to claim 4, wherein the second position measurement sensor is a pressure sensor.

7. The device according to claim 4, wherein the first oxygen measurement sensor has a receiver and two light-generating and light-transmitting systems, whose beam paths are arranged at an angle symmetrically to the vertical axis.

8. The device according to claim 4, wherein each light-generating and light-conducting system can be adjusted by adjusting means and fixed by clamping means at an angle, wherein one system generates and conducts red light and the other system generates and conducts infrared light, a system comprising, in each instance, within a tube, an objective lens, collimating objective lenses and light sources, wherein each tube has an ankle joint in the region of the objective lens, wherein the receivers are arranged parallel to the vertical axis in a receiver housing which has the ankle joints and which is arranged symmetrically with respect to the vertical axis, wherein each system is connected with the ankle joint of the tube and is supported in the ankle joints of the receiver housing so as to be swivelable relative to the vertical axis, and wherein a cover for screening out extraneous light is associated with the light-generating and light-conducting systems and with the receivers.

9. The device of claim 4 wherein the first oxygen measurement sensor and the second position measurement sensor are detachably connected to one another.

10. The device according to claim 9, wherein the measurement sensor and the first oxygen measurement sensor form a constructional unit which can be placed on a catheter.

11. The device according to claim 9, wherein the second position measurement sensor and the first oxygen measurement sensor form a unit which is integrated in the distal end of the catheter.

12. The device according to claim 9, wherein means for aligning the beam axes of the first oxygen measurement sensor and/or the beam axes of the additional measurement sensor are arranged in the catheter.

13. A method for the non-invasive in vivo determination of oxygen saturation in human blood vessels and organs comprising:
   a) providing a first oxygen measurement sensor having at least two light sources of different wavelengths and at least one receiver therefor;
   b) providing a second position measurement sensor comprising a sonography transmitter-receiver which emits ultrasonic waves, which forms a constructional unit with the first oxygen measurement sensor;
   c) locating a specific position external to but adjacent to a predetermined vessel or organ with the second position measurement sensor;
   d) positioning the first oxygen measurement sensor at the specific position and monitoring the position with the second position measurement sensor;
   e) radiating light from the light sources on the blood vessel or organ, such that the light which is transmitted by oxygen particles bonded with hemoglobin in the irradiated blood vessel or organ and reflected by the surrounding tissue is received by the receiver;
   f) converting the reflective light received by the receiver into an electrical signal that is proportional to the intensity of the reflected light;
   g) transmitting the electrical signal to a pulsoximeter to determine the oxygen saturation in the blood vessel or organ.

* * * * *